(12) United States Patent
    Spearman-White et al.

(10) Patent No.: US 12,638,672 B2
(45) Date of Patent: May 26, 2026

(54) IMAGING ELEMENT CLEANING APPARATUS WITH SINGLE HAND OPERABILITY

(71) Applicant: ClearCam, Inc., Austin, TX (US)

(72) Inventors: Tremaan Alexander Spearman-White, Austin, TX (US); Etse-Oghena Campbell, Austin, TX (US); Christopher Robert Idelson, Austin, TX (US)

(73) Assignee: ClearCam, Inc., Austin, TX (US)

( * ) Notice: Subject to any disclaimer, the term of this patent is extended or adjusted under 35 U.S.C. 154(b) by 138 days.

(21) Appl. No.: 18/742,938

(22) Filed: Jun. 13, 2024

(65) Prior Publication Data

US 2025/0383540 A1    Dec. 18, 2025

(51) Int. Cl.
    *A61B 90/70*      (2016.01)
    *A61B 1/00*      (2006.01)
    *B08B 1/32*      (2024.01)
    *G02B 27/00*      (2006.01)

(52) U.S. Cl.
    CPC ...... *G02B 27/0006* (2013.01); *A61B 1/00131* (2013.01); *A61B 90/70* (2016.02); *B08B 1/32* (2024.01); *A61B 2090/701* (2016.02)

(58) Field of Classification Search
    CPC ................ A61B 1/121–122; A61B 1/126–127
    See application file for complete search history.

(56) References Cited

U.S. PATENT DOCUMENTS

| | | |
|---|---|---|
| 5,392,766 A | 2/1995 | Masterson et al. |
| 5,518,502 A | 5/1996 | Kaplan et al. |
| 5,695,448 A | 12/1997 | Kimura et al. |
| 6,755,782 B2 | 6/2004 | Ogawa |
| 6,905,078 B1 | 6/2005 | Gattuso et al. |

(Continued)

FOREIGN PATENT DOCUMENTS

| | | |
|---|---|---|
| CN | 101883531 B | 7/2014 |
| EP | 0647425 A1 | 4/1995 |

(Continued)

OTHER PUBLICATIONS

International Search Authority, Notification of Transmittal of the International Search Report and Written Opinion of the International Search Authority, PCT/US2025/32946, 20 pages.

*Primary Examiner* — Matthew J Kasztejna
(74) *Attorney, Agent, or Firm* — David O. Simmons; IVC Patent Agency

(57)    ABSTRACT

Embodiments of the disclosures made herein are directed to providing an effective and reliable approach for cleaning an exposed surface of an imaging element (e.g., a lens) of apparatuses including but not limited to medical imaging instruments such as endoscopes and laparoscopes and the like. In the case of medical imaging instruments, cleaning apparatuses configured in accordance with embodiments the disclosures made herein can be cleaned while the distal end portion of the endoscope is in vivo. Such apparatuses have a cleaning member incorporated therein (e.g., a resilient polymeric wiper, a sponge, an absorbent pad or the like) that is used for cleaning the exposed surface of the imaging element. The apparatus is preferably adapted for being mounted on imaging apparatus but can also be entirely or partially integral with one or more components of the imaging apparatus or system of which it is a component.

21 Claims, 11 Drawing Sheets

(56) References Cited

U.S. PATENT DOCUMENTS

| | | | |
|---|---|---|---|
| 6,923,759 | B2 | 8/2005 | Kasahara et al. |
| 7,543,314 | B2 | 6/2009 | Kadykowski |
| 7,959,561 | B2 | 6/2011 | Akui et al. |
| 8,690,764 | B2 | 4/2014 | Clark et al. |
| 8,979,738 | B2 | 3/2015 | Hsu et al. |
| 9,050,036 | B2 | 6/2015 | Poll et al. |
| 9,486,129 | B2 | 11/2016 | Rodriguez Sanjuan |
| 9,763,567 | B2 | 9/2017 | O'Prey et al. |
| 10,791,918 | B1 | 10/2020 | Gilkey et al. |
| 2009/0229067 | A1 | 9/2009 | Becker et al. |
| 2009/0250081 | A1 | 10/2009 | Gordin et al. |
| 2012/0101338 | A1 | 4/2012 | O'Prey et al. |
| 2014/0094650 | A1 | 4/2014 | Schaning |
| 2016/0128551 | A1 | 5/2016 | Hsu et al. |
| 2016/0143512 | A1 | 5/2016 | Cheng et al. |
| 2017/0332893 | A1 | 11/2017 | Irion et al. |
| 2017/0367571 | A1 | 12/2017 | Nave |
| 2022/0175236 | A1 | 6/2022 | Idelson et al. |

FOREIGN PATENT DOCUMENTS

| | | | |
|---|---|---|---|
| JP | S5861723 | A | 4/1983 |
| JP | H01204637 | A | 8/1989 |
| JP | 04-362912 | | 12/1992 |
| JP | H05103748 | A | 4/1993 |
| JP | 2015031026 | A | 2/2015 |
| JP | 5735908 | B2 | 6/2015 |
| WO | 200912587 | A2 | 10/2009 |
| WO | 2014034839 | A1 | 3/2014 |
| WO | WO2017006684 | | 12/2017 |
| WO | 2020112852 | A1 | 4/2020 |

-Prior Art-

1

A1

125

LP

103

111

8A

8A

102

106

10, 25

102

106

10, 25

L1

116

114

-Prior Art-

-Prior Art-

IMAGING ELEMENT CLEANING APPARATUS WITH SINGLE HAND OPERABILITY

FIELD OF THE DISCLOSURE

The disclosures made herein relate generally to cleaning of devices that utilize a remote imaging element for visualization of structures at a concealed site and, more particularly, to an imaging element cleaning apparatus for cleaning an exposed surface of the imaging element such as, for example, while the exposed surface is located within a concealed site such as an in vivo human or animal environment. The disclosed imaging element cleaning apparatus are beneficially configured for enabling single hand operability for instances of imaging element cleaning operation.

BACKGROUND

Surgical procedures utilizing in vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization device for providing in vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope" and may be in the form of a scope having an integral video camera (i.e., a videoscope).

As shown in FIG. 1, an endoscope 1 used in these surgical procedures is characterized as having a user interface portion 5 and an extension portion 10 connected at its proximate end 15 to the user interface portion 5. Scopes for endoscopic surgery generally have an extension portion that is substantially flexible, whereas scopes for other types of surgical procedures—e.g., for laparoscopic surgery, as shown in FIG. 1—generally have an extension portion 10 that is substantially rigid. The extension portion 10 has an imaging element 20 such as a lens at its distal end portion 25. The imaging element 20 can have an exposed surface that is typically flush with or that defines an end face of the extension portion 10. However, in some embodiments, the imaging element 20 may be recess within or protruding from an end face of the extension portion 10. The imaging element 20 may be connected to an optical fiber or other image transmitting element that is internal to the endoscope 1. The optical fiber or other image transmitting element may extend along the length of the extension portion 10 and terminates at signal processing unit (not shown) within the endoscope 1 (e.g., within a housing defining the user interface portion 5). The imaging element 20 may be that of a camera such as where the endoscope 1 is embodied as a videoscope.

During a surgical procedure using an endoscope, the exposed surface of the imaging element may become compromised from an optical standpoint due to one or more in vivo scenarios. Examples of these scenarios include the exposed surface of the imaging element becoming fogged with moisture within the surgical space and the exposed surface of the imaging element may be smeared by blood or other bodily fluids or tissues (e.g., interstitial fluid, fat tissue or the like). Currently, there are two primary different endoscope cleaning methods that are commonly utilized.

The first of these cleaning methods is to remove the endoscope from the body, wipe the imaging element clean, and reinsert the endoscope into the body. This method, though effective, is time consuming and causes the surgeon to lose visual of the surgical site and flow of the operative procedure, which can be considered dangerous, as surgical instruments typically remain inside the body. This method may also subject the patient to a higher risk of infection. The second of these cleaning methods is to wipe the exposed surface of the imaging element upon a nearby organ or tissue in vivo. Although the endoscope remains inside the body, takes less time to clean and does not potentially compromise the surgical site, this method is often not sufficiently effective either due to the "cleaning" surface not providing effective cleaning performance or simply further compromising the exposed surface of the imaging element. Also, when using either of these cleaning methods, the surgeon must undesirably spend time relocating the endoscope back to the surgical site after cleaning the imaging element.

At a minimum, current approaches for cleaning the exposed surface of the imaging element can be a hindrance and an annoyance for surgeons and may offer poor cleaning performance. Additionally, the action of cleaning the exposed surface of the imaging element increases the length of time a surgical procedure takes, thereby decreasing the amount of operating room (OR) time available to the hospital or other type of surgical facility. It is also costly for surgical facilities, patients, and insurance companies due to wasted time, and possibly surgical complications and post-surgical infection rates. Additionally, as patients undergo longer procedures, their time spent under anesthesia increases which has been shown to correlate to a rise in surgical complication rates and post-surgical infection rates. Thus, the added time associated with current commonly used approaches for cleaning the exposed surface of the imaging element is not only a hindrance, but also potentially medically and financially costly.

Thus, to maintain required visualization of target surgical sites, it is desirable to clean an exposed surface of an imaging element of a device while the distal end portion of the device that carried an imaging element remains in a concealed operation site (e.g., an endoscope in vivo). Known methods and devices that are intended to provide for cleaning of a surface of such devices when still within the concealed operation site (e.g., an endoscope in vivo) have one or more shortcomings (e.g., lack efficacy, interfere with the surgical procedure such as by requiring two-handed operability, require significant alteration to a surgeon's preferred surgical technique, etc.). Therefore, an effective, efficient, simple and reliable approach for enabling an exposed surface of an imaging element of a visualization device (e.g., an endoscope) to be cleaned while the distal end portion of apparatus is still within the concealed operation site (e.g., in vivo) would be advantageous, desirable and useful.

SUMMARY OF THE DISCLOSURE

Embodiments of the disclosures made herein are directed to providing an effective and reliable approach for allowing an exposed surface of an imaging element (e.g., a lens) of a device (e.g., an endoscope) be cleaned while the distal end portion of the device is within a concealed operational site (e.g., in vivo). More specifically, one or more embodiments of the disclosures made herein provide an apparatus for use with an endoscope utilized in one or more types of surgical procedures (e.g., endoscopic surgery, laparoscopic surgery, thoracoscopic surgery and the like), The apparatus incorporates a cleaning member (e.g., a resilient polymeric wiper, a sponge, an absorbent pad or the like) that is used for cleaning the exposed surface of the imaging element of the device while the imaging element is within the concealed operation site. The apparatus is preferably adapted for having the device mounted thereon but can also be entirely or partially integral with one or more components of a system (e.g., a robotic arm configured for carrying, operating and manipulating an endoscope).

Cleaning apparatuses in accordance with the disclosures made herein are configured for enabling single hand operability for instances of imaging element cleaning operation. Such single hand operability is a beneficial attribute adding valuable end-user functionality. For example, endoscopes are usually manipulated by a surgeon during a surgical procedure using a single hand. Accordingly, it is beneficial for cleaning apparatuses in accordance with the disclosures made herein, with which endoscopes are engaged for enabling in vivo cleaning of the imaging element of the endoscope, to provide for single hand operability for instances of imaging element cleaning operation.

In one or more embodiments of the disclosures made herein, an imaging element cleaning apparatus comprises a chassis, a cleaning member, a coupling element, and a cleaning member movement mechanism. The chassis is engageable with an endoscope to retain the endoscope in a fixed seated position relative to the chassis. The cleaning member is at a distal end portion of the chassis. The coupling element is attached at a distal end portion thereof to the cleaning member whereby rotational movement of the coupling element causes corresponding rotational movement of the cleaning member. The cleaning member movement mechanism is at a proximate end portion of the chassis. The cleaning member movement mechanism includes a rotational movement body and a linear movement body moveably coupled to the rotational movement body. The rotational movement body and the linear movement body are jointly configured whereby linear movement of the linear movement body from an at-rest position to a fully-displaced position and back to the at-rest position causes the rotational movement body to correspondingly rotate in a first rotational direction from a first rotational position to a second rotational position and back to the first rotational position. The rotational movement body is coupled to a proximate end portion of the coupling member for enabling the rotation of the rotational movement body to correspondingly cause the rotational movement of the coupling element.

In one or more embodiments of the disclosures made herein, an imaging element cleaning apparatus comprises a chassis, a cleaning member, a coupling element, and a cleaning member movement mechanism. The chassis is engageable with an endoscope to retain the endoscope in a fixed seated position relative to the chassis. The cleaning member is at a distal end portion of the chassis. The coupling element is attached at a distal end portion thereof to the cleaning member whereby rotational movement of the coupling element causes a corresponding rotational movement of the cleaning member. The cleaning member movement mechanism is at a proximate end portion of the chassis. The cleaning member movement mechanism includes a rotational movement body and a linear movement body moveably coupled to the rotational movement body. The rotational movement body includes a groove extending around an outer surface of the rotational movement body. The linear movement body includes an engagement member positioned within the groove. The linear movement body is biased to an at-rest position, is constrained to linear movement, and is moveable along an axial reference axis between the at-rest position and a fully-displaced position. The groove is bound by a first perimeter edge portion thereof and a second perimeter edge portion thereof. Movement of the linear movement body toward the fully-displaced position causes the linear movement body to engage the first perimeter edge portion and movement of the linear movement body away from the fully-displaced position causes the linear movement body to engage the second perimeter edge portion. A profile of the first perimeter edge portion and a profile of the second perimeter edge portion jointly enable linear movement of the linear movement body from the at-rest position to the fully-displaced position and back to the at-rest position to cause the rotational movement body to correspondingly rotate in a first rotational direction from a first rotational position to a second rotational position and back to the first rotational position. The rotational movement body is coupled to a proximate end portion of the coupling member for enabling the rotation of the rotational movement body to corresponding causes the rotational movement of the coupling element.

In one or more embodiments, the rotational movement body is coupled to the linear movement body though a camming structure that defines rotational movement of the rotational movement body as a function of linear displacement of the linear movement body.

In one or more embodiments, the rotational movement body includes a groove extending contiguously around an outer surface of the rotational movement body, a contour of the groove defines rotational movement of the rotational movement body as a function of linear displacement of the linear movement body, and an engagement member of the linear movement body is positioned within the groove.

In one or more embodiments, the cleaning member movement mechanism includes a control lever having a first end portion, a second end portion, and a central portion between the first end second end portions, the cleaning member movement mechanism includes a main mounting body one of engaged with the chassis and unitarily formed with the chassis, the control lever is pivotably engaged at the first end portion thereof to at least one of the chassis and the main mounting body, and the control lever is pivotable coupled at the central portion thereof to the linear movement body.

In one or more embodiments, the cleaning member movement mechanism includes a control lever linkage member and the control lever is pivotable engaged at the central portion thereof to the linear movement body by the control lever linkage member.

In one or more embodiments, the linear movement body is constrained to linear movement along an axial reference axis and at least one of a main mounting body of the cleaning member movement mechanism, the chassis, and the linear movement body constrains rotational movement of the rotational movement body to being about the axial reference axis.

In one or more embodiments, the cleaning member movement mechanism includes a main mounting body engaged with the chassis or unitarily formed with the chassis, the linear movement body is constrained to linear movement along an axial reference axis, and the main mounting body and/or the linear movement body constrains rotational movement of the rotational movement body to being about the axial reference axis.

In one or more embodiments, the rotational movement body being coupled to the proximate end portion of the coupling member includes the rotational movement body being attached directly to the proximate end portion of the coupling member.

In one or more embodiments, the rotational movement body is slidably engaged with the linear movement body for enabling axial translation along the axial reference axis, axial translation of the linear movement body from the at-rest position to the fully-displaced position causes the rotational movement body to axially translate from a first position placing the cleaning member in a stowing position to a second position placing the cleaning member in a deployed position, and axial translation of the linear movement body from the fully-displaced position to the at-rest position causes the rotational movement body to axially translate from the second position to the first position.

In one or more embodiments, the rotational movement body is a two part body including a first body part and a second body part, the first body part of the rotational movement body is coupled to the linear movement body though a camming structure that defines rotational movement of the first body part of the rotational movement body as a function of linear displacement of the linear movement body, the first body part is moveably coupled to the second body part for enabling relative axial displacement therebetween, axial translation of the linear movement body from the at-rest position to the fully-displaced position causes the second body part of the rotational movement body to axially translate from a first position placing the cleaning member in the stowing position to a second position placing the cleaning member in the deployed position; and axial translation of the linear movement body from the fully-displaced position to the at-rest position causes the second body part of the rotational movement body to axially translate from the second position to the first position.

These and other objects, embodiments, advantages and/or distinctions of the present invention will become readily apparent upon further review of the following specification, associated drawings and appended claims.

DETAILED DESCRIPTION

Figure 1:
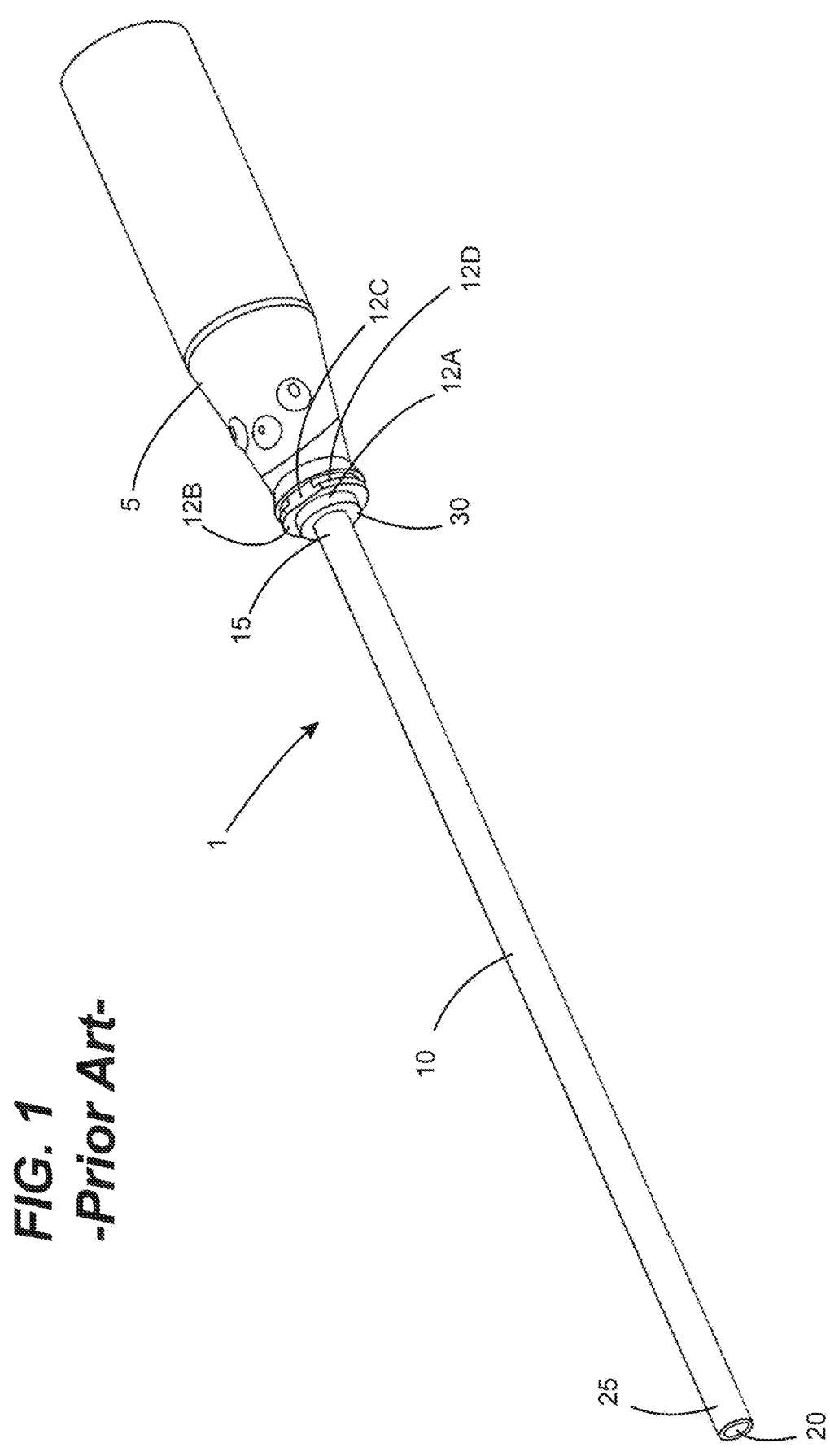
FIG. 1 is a perspective view showing a prior art endoscope, which is embodied as a wireless videoscope.
Figures 2, 3:
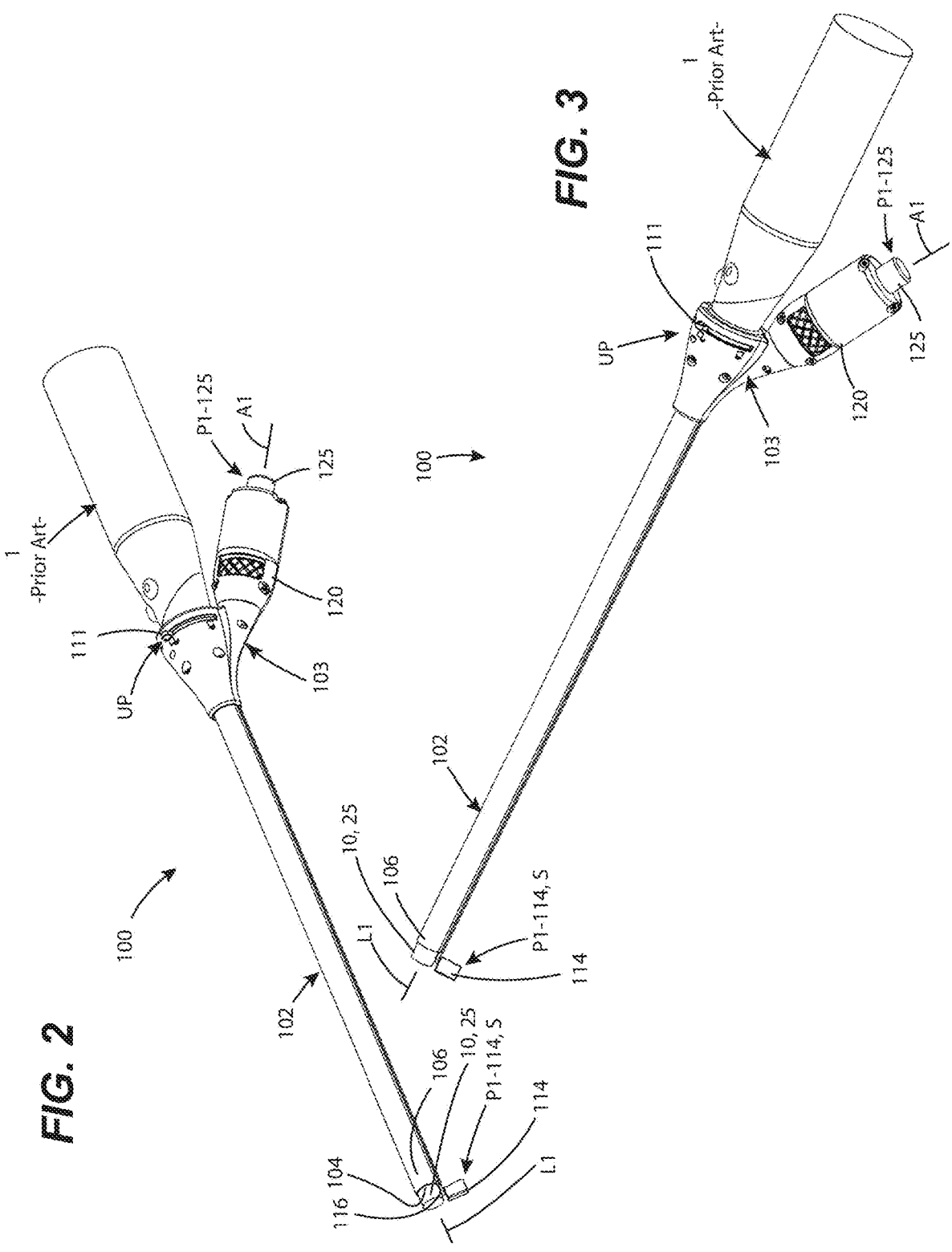
FIG. 2 is a first perspective view showing an imaging element cleaning apparatus in accordance with a first embodiments of the disclosures made herein, where a cleaning member of the imaging element cleaning apparatus is in a stowed axial position and a home rotational position.
FIG. 3 is a second perspective view of the imaging element cleaning apparatus shown in FIG. 2, where the cleaning member is in the stowed axial position and the home rotational position.

FIGS. 2-9 illustrate various aspects of an imaging element cleaning apparatus configured in accordance with a first embodiment of the disclosures made herein, which is designated as the cleaning apparatus 100. Cleaning apparatus 100 is preferably, but not necessarily, configured to be used with commercially available (i.e., prior art) endoscopes, such as endoscope 1 of FIG. 1 for cleaning an imaging element thereof (i.e., an imaging element cleaning apparatus). Examples of such commercially available endoscopes include, but are not limited to, endoscopes manufactured under brand names of Karl Storz, Linvatec, Olympus, Richard Wolf, Stryker and Intuitive Surgical (i.e., DaVinci). To this end, in preferred embodiments, the cleaning apparatus 100 can be engineered as endoscope-specific for one or more given models of one or more manufacturers based on the dimensional attributes of such commercially available endoscopes. An underlying consideration of the manner in which the cleaning apparatus 100 is engineered for intended brands and/or models of endoscope is that there be a high level of dimensional precision between the endoscope and the cleaning apparatus. Such dimensional precision can be characterized to include both the inhibition of any unacceptable level of relative movement between the endoscope and the cleaning apparatus 100 and relative placement of key structural elements of the endoscope relative to those of the cleaning apparatus 100.

The cleaning apparatus 100 has an elongated body 102 that is adapted to have the extension portion 10 of the endoscope 1 inserted therein such that the endoscope 1 is in a fixed seated position relative to the cleaning apparatus 100 (i.e., relative to a chassis thereof). In such fixed seated position, a dimensionally predictable surface or feature of the endoscope 1 abuts a mating dimensionally predictable surface or feature of the endoscope cleaning apparatus 100. This mating surface or feature of the cleaning apparatus 100 serves as a reference structure of the cleaning apparatus 100. With the endoscope 1 in this fully seated position on the cleaning apparatus 100 with respect to the reference structure, a distal end portion 25 of the endoscope 1 (i.e., distal end portion of the extension portion 10) protrude from within an opening 104 in the distal end portion 106 of the elongated body 102 by a known, predictable amount. This fully seated position preferably also includes a positioning of the endoscope 1 angularly (i.e., anti-rotationally) relative to the chassis (e.g., relative to a centerline longitudinal axis L1 of the elongated body 102). Through such an interfacial arrangement and dimensional tolerances, a high level of dimensional precision between the endoscope 1 and the cleaning apparatus 100 can be achieved. Such dimensional precision is beneficial to the cleaning performance afforded by the cleaning apparatus 100. As is known in the art, a cleaning apparatus may include a structural mechanism for enable placement of the endoscope 1 relative to the cleaning apparatus 100 when in the fixed seated position to be adjusted.

As discussed above in reference to FIG. 1, the distal end portion 25 of the endoscope 1 carries the imaging element 20 (e.g., a lens). The imaging element 20 is exposed at and is generally flush with or defines an end face at the distal end portion 25 of the extension portion 10 of the endoscope 1. The distal end portion 25 of the endoscope 1 is exposed at the opening 104 in the distal end 106. As a result of the seated placement of the endoscope 1 on the cleaning apparatus 100, the imaging element 20 is at a known and predictable position relative to the reference structure of the cleaning apparatus 100. Thus, for an endoscope engineered for use with a specific cleaning apparatus, the components of the cleaning apparatus 100 can similarly be at known and predictable position relative to structures of the endoscope 1, thereby providing for precise placement and configuration of components of the cleaning apparatus 100 to achieve a desired and predictable level of cleaning performance.

The chassis can include a plurality of structural elements that provide for the known and predictable position of the endoscope 1 when mounted in a seated position on the chassis. For example, one of these structural elements may be the effective inside diameter (e.g., for ribbed or textured interior surface) or the actual inside diameter (e.g., a smooth interior wall) of the elongated body 102 in relation to an outside diameter of the extension portion 10 of the endoscope 1 and the elongated body 102 of the chassis. It is preferable to maintain a close fit between the outside wall of elongated body 102 and the mating exterior wall of the extension portion 10 so as to provide for a fluid-resistant interface between the elongated body 102 and the extension portion 10 and to limit off-axis pitch between a longitudinal axis of the elongated body 102 and the extension portion 10.

Another one of these structural elements is a seating structure 112 (FIG. 8A) on the user interface body 103. In some embodiments, the seating structure 112 can include a first surface 112A that engages a mating first surface 12A of the scope 1, a second surface 112B that engages a mating second face surface 12B of the scope 1, and a third surface 112C that engages a mating third surface 12C of the scope 1. The first surface 112A may be an interior cylindrical surface that serves to define alignment of the endoscope 1 radially relative to a centerline longitudinal axis L1 of the elongated body 102 (i.e., limiting radial movement relative to the cleaning apparatus calibration device shown in FIG. 8). The second surface 112B is a planar surface (e.g., extending perpendicular to the centerline longitudinal axis L1) that serves to define positioning of the endoscope 1 axially relative to the centerline longitudinal axis L1 of the elongated body 102. The third surface 112C is a planar surface (e.g., extending tangentially offset from the centerline longitudinal axis L1) that serves to define positioning of the endoscope 1 angularly (i.e., anti-rotationally) relative to the centerline longitudinal axis L1 of the elongated body 102. The first surface 112A may be that of a cylindrical recess bound at the top by the second surface 112B. The third surface 112C may be a flat planar surface that extends offset from and parallel to the centerline longitudinal axis L1. In these regards, the seating structure 112 positions the endoscope 1 in a predictable seated orientation (i.e., a known reference configuration/position) relative to the elongated body 102 and the user interface body 103.

The elongated body 102 and a user interface body 103 at a proximate end portion of the elongated body 102 jointly define the chassis of the cleaning apparatus 100. The chassis serves as the platform on which the endoscope 1 can be mounted in a predictable seated position. It is disclosed herein that the chassis can be that of a robot that provides robot-assisted surgery or can be adapted to operatively interface with a mating mounting portion of such a robot. For example, the elongated body 102 and/or the user interface body 103 can be that of an arm or other structure of the robot or adapted to operatively interface with an instrument mounting portion of the arm of the robot.

The elongated body 102 can be a tube (e.g., a sheath) having a central passage 110 (shown in FIG. 8A) with a round or generally round cross-sectional shape. Alternatively, the elongated member 102 can be a non-tubular structure such as a skeletal structure that engages the extension portion 10 of the endoscope at discrete spaced-apart locations thereof. The central passage 110 has a size and profile that is adapted to have the extension portion 10 of the endoscope 1 seated therein by inserting the extension portion 10 into the central passage 110 and sliding the extension portion 10 along the length of the elongated body 102 until the endoscope 1 is in a seated position S1 on the chassis.

The user interface body 103 can include a retention member 111 that engages a mating structural feature of the endoscope 1 for securing the endoscope 1 is in a fixed seated position relative to the chassis. The retention member 111 is moveably mounted on the interface body 103 for enabling the endoscope 1 to be selectively secured to the cleaning apparatus 100 in the aforementioned predictable seated orientation. The retention member 111 is disposed within a channel 115 of the user interface body 103 and is movable (e.g., manually movable about the centerline longitudinal axis L1) between an unlocking position UP and a locking position LP. In the unlocking position UL, the endoscope 1 may be engaged with (i.e., predictable seated orientation) and disengaged from the cleaning apparatus 100. In the locking position LP, the endoscope 1 is in secured engagement (i.e., predictable seated orientation) with the cleaning apparatus 100. For example, when the retention member 111 is in the unlocking position UP, a scope engagement portion 111A of the retention member 111 (e.g., and inwardly protruding shoulder) is in alignment with a mating portion of the third surface 12C of the endoscope 1 to thereby provide clearance with the mating portion of the third surface 12C of the endoscope 1 for permitting the endoscope 1 to be engaged with and disengaged from the cleaning apparatus 100. When the retention member 111 is in the locking position LP, the scope engagement portion 111A of the retention member 111 abuts (i.e., lies in front of as viewed from the user interface body 103) a flange 12D of the endoscope 1 that defines the second surface 12B of the endoscope 1, thereby inhibiting the endoscope 1 from being disengaged from engagement with the cleaning apparatus 100.

Figure 8A:
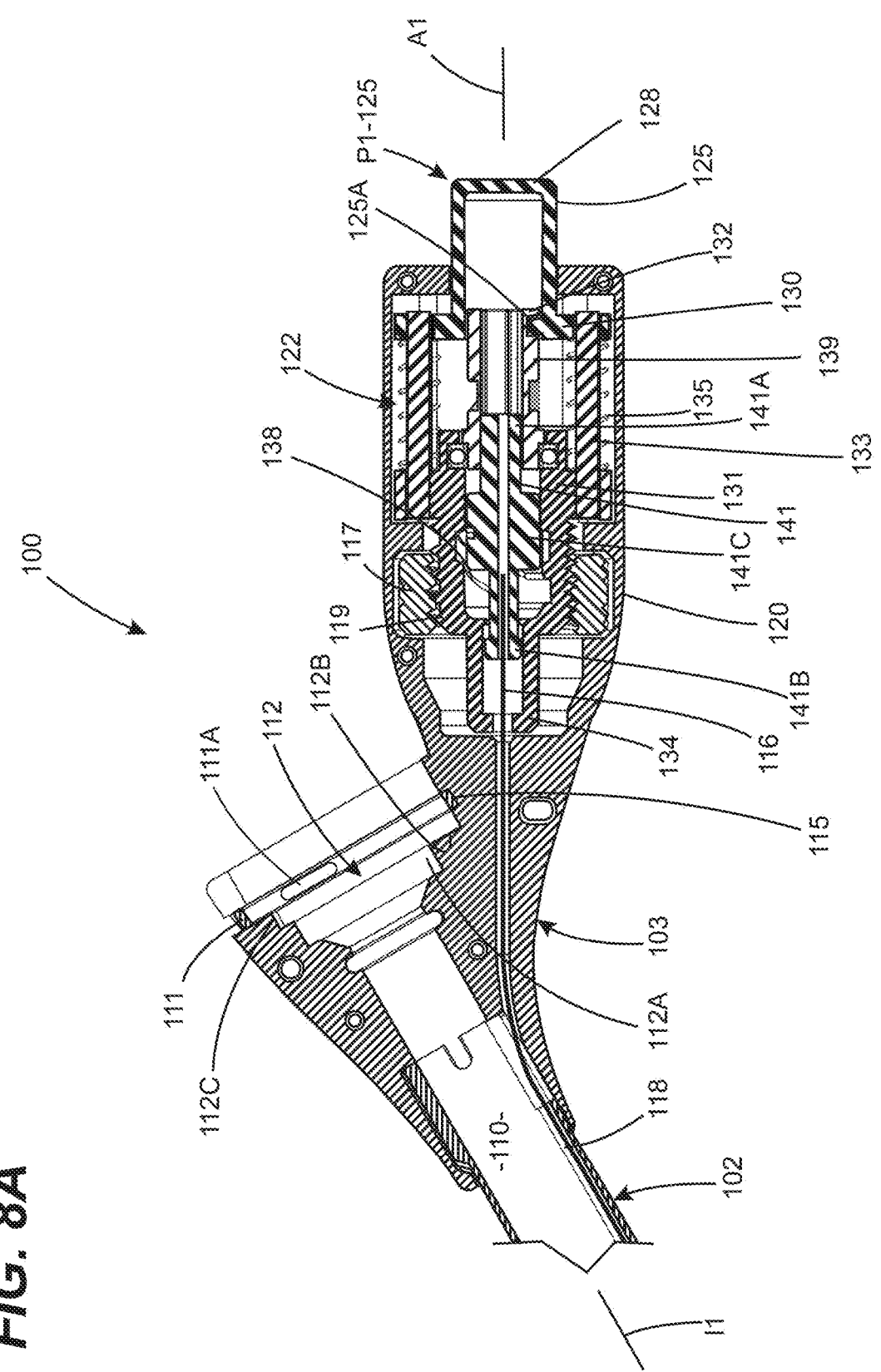
FIG. 8A is a cross-sectional view taken along the line 8A-8A in FIG. 5.

The cleaning apparatus 100 includes a cleaning member 114 adjacent to the opening 104 in the distal end portion 106 of the elongated body 102. The anti-rotation functionality discussed above in reference to the seating structure 112 serves to define angular positioning (clocked position) of the endoscope 1 relative to the cleaning member 114 about the centerline longitudinal axis L1. As discussed below in greater detail, the cleaning member 114 functions to clean contaminants and debris from an exterior surface of the imaging element 20. The cleaning member 114 can be fixedly attached to a distal end portion of a coupling element 116 whereby rotational movement of the coupling element 116 causes corresponding rotational movement of the cleaning member 114. As best shown in FIG. 8A, the coupling element 116 may extend through a central passage of a channel 118 of the elongated body 102. Preferably, the central passage of the channel 118 and the central passage 110 of the elongated body 102 extend parallel to each other.

In some embodiments, the coupling element 116 is characterized by an elongated small diameter structure that offers at least a limited degree of bendability in combination with high torsional rigidity. In other embodiments, the coupling element 116 is characterized by an elongated small diameter structure that offers a given amount of torsional compliance. Based on these characterizing attributes, examples of coupling element 116 include, but are not limited to, solid metallic wire, spiraled metal wire, a polymeric filament(s), a composite filament(s), or the like.

The user interface body 103, which can be configured as a handle for the cleaning apparatus 100, includes a cleaning member controller 120 that comprises a cleaning member movement mechanism 122 (FIG. 8A) that is coupled to the cleaning member 114 by the coupling element 116. The cleaning member movement mechanism 122 enables selective movement of the cleaning member 114 to provide for selective movement of the cleaning member 114 relative to the distal end portion 106 of the elongated body 102 and co-located imaging element 20 of the endoscope 1 to perform cleaning of the imaging element 20.

Figures 6, 7:
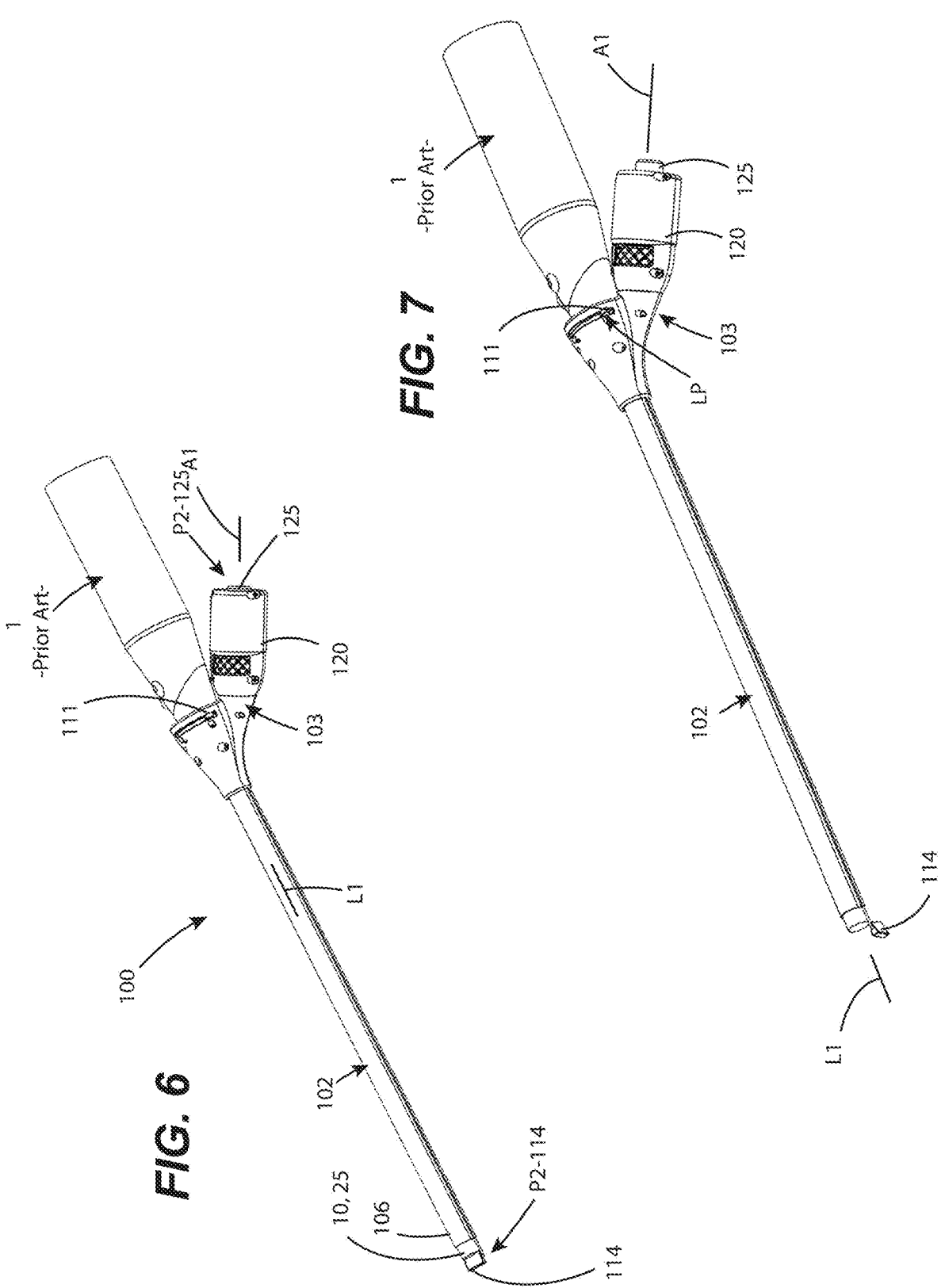
FIG. 6 is a perspective view of the imaging element cleaning apparatus shown in FIG. 2, where the cleaning member is in the deployed axial position and a fully-displaced rotational position.
FIG. 7 is a perspective view of the imaging element cleaning apparatus shown in FIG. 2, where the cleaning member is in the deployed axial position and a post-cleaning intermediate rotational position.

The cleaning member movement mechanism 122 includes a control body 125 that is constrained to linear movement along to an axial reference axis A1. The control body is in the form of a button that is preferably engaged with the thumb of a user of the cleaning apparatus 100. The control body 125 extends from an end face of the cleaning member controller 120. Placement and movement of the control body 125 provides the cleaning apparatus 100 with single hand lens cleaning. Endoscopes are usually manipulated by a surgeon during a surgical procedure using a single hand. Accordingly, single hand operation of the cleaning apparatus 100 and the endoscope 1 as engaged with the cleaning apparatus 100 is beneficial and desirable. To this end, the control body 125 is moveable (e.g., manually) between an at-rest position P1-125 (FIGS. 2-3) and a fully-displaced position P2-125 (FIG. 6). In preferred embodiments, the control body 125 is biased (e.g., via one or more resilient members such as springs) to the at-rest position P1-125. In operation, linear movement of the control body 125 from the at-rest position P1-125 to the fully-displaced position P2-125 and back to the at-rest position P1-125 causes the cleaning member 114 to correspondingly rotate in a first rotational direction from a home rotational position P1-114 (FIGS. 2-3) to a displaced rotational position P2-114 (FIG. 6) and back to the home rotational position P1-114.

In some embodiments, as shown in FIGS. 2-5, movement for providing an instance of imaging element cleaning by the cleaning member 114 includes the cleaning member 114 moving axially from a stowed axial position S (FIGS. 2-3) to a deployed axial position D (FIG. 4-5) relative to the distal end position 106 of the elongated body 102, where the cleaning member 114 returns to the stowed axial position S in conjunction with returning to the home rotational position P1-114. The deployed axial position D is a position in which the cleaning element 114 is at, near or beyond a terminal end of the endoscope 1 (e.g., an exterior surface of the imaging element 20). The stowed axial position S is a position in which the cleaning element 114 is retracted from the deployed axial position D (e.g., by a maximum distance of travel therebetween). One benefit of the cleaning member 114 being in the stowed axial position S in between instances of cleaning the member wiping 114 may be that the cleaning member 114 is fully outside of the field of view of the imaging element 20 or is suitably removed from a primary region of such field of view. Another benefit of the cleaning member 114 being in the stowed axial position S in between instances of cleaning the member wiping 114 may be that the cleaning member 114 is less prone to come into contact with tissue, organs, or the like manipulation of the endoscope 1 during a surgical procedure.

Figure 8B:
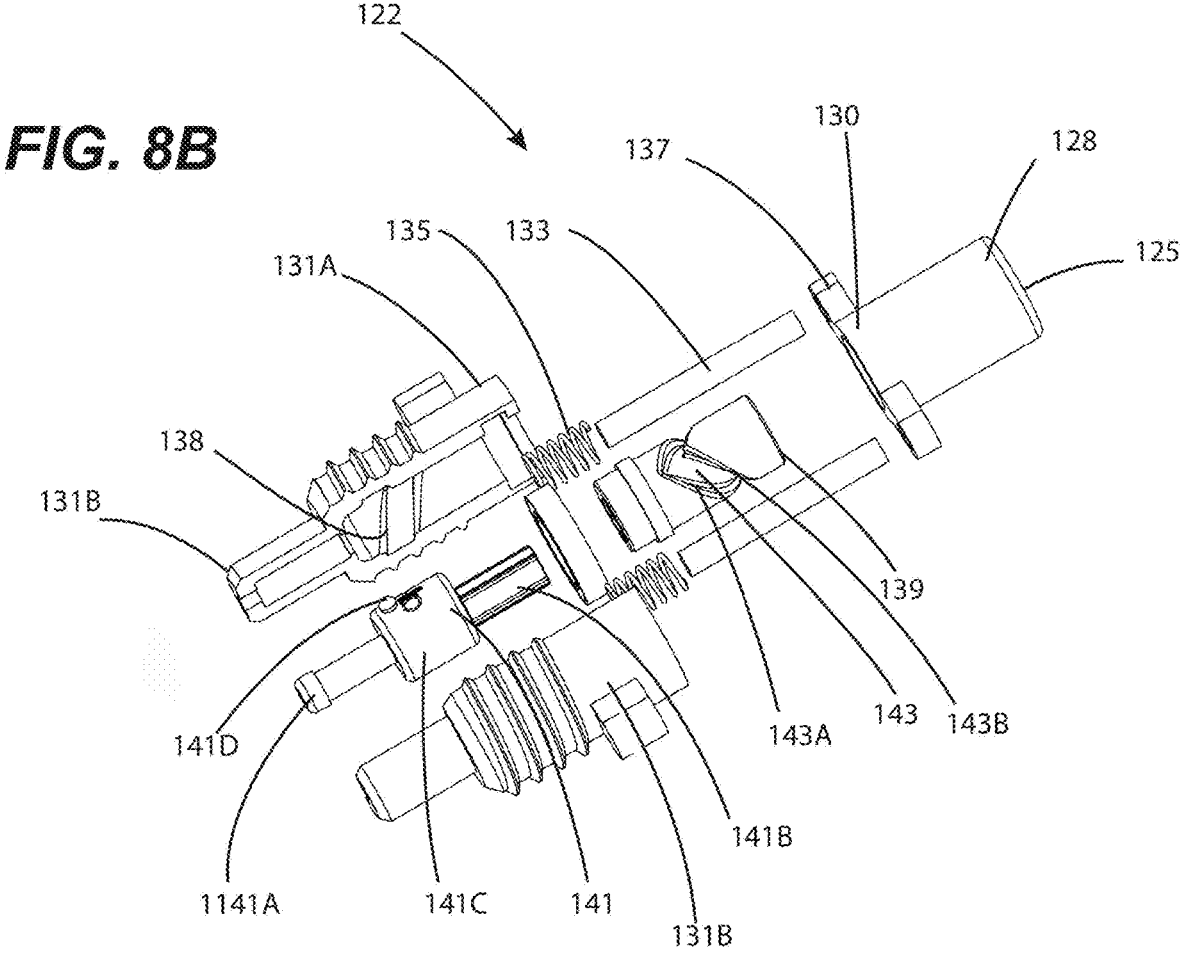
FIG. 8B is an exploded view of cleaning member movement mechanism components shown in FIG. 8A.

Referring now, to FIGS. 8A and 8B, aspects of a specific implementation of the cleaning member movement mechanism 122 are disclosed. The control body 125 includes a user interface portion 128 and a mounting portion 130 connected to the user interface portion 128. The mounting portion 130 is translatably engaged with a main mounting body 131 of the cleaning member movement mechanism 122. The main mounting body 131 may be a discrete component that is engaged with the chassis (e.g., a user interface housing thereof) or may be unitarily formed with the chassis. The main mounting body 131 is located within an interior space of the user interface body 103 and is fixedly engaged with the user interface body 103. As shown, the main mounting body 131 includes opposing body portions 131A and 131B. In some embodiments, the main mounting body 131 may be a one-piece body. To accommodate the need for fine adjustment of the cleaning element 114 relative to the distal end portion 106 of the elongated body 102, the cleaning apparatus 100 may include a dial 117 that is threadedly engaged with a mating threaded portion 119 of the main mounting body 131 whereby rotation of the dial 117 provides for a corresponding and proportional axial movement of the main mounting body 131 relative to a fixed reference point of the user interface body 103. Because the cleaning member 114 is coupled to the main mounting body by the coupling element 116, movement of the main mounting body results in a corresponding axial adjustment of cleaning member 114.

The cleaning member movement mechanism 122 includes guide members 133 and springs 135 (i.e., resilient biasing members). The guide members 133 are in a spaced-apart arrangement and are each engaged with a respective one of the opposing body portions 131A and 131B of the main mounting body 131. Each of the springs 135 is associated with one of the guide members 133. The mounting portion 130 of the control body 125 is engaged with the guide members 133 and the springs 135 to jointly bias the control body 125 to the at-rest position P1-125. Engagement of the mounting portion 130 of the control body 125 with the guide members 133 constrains movement of the control body 125 to being along the axial reference axis A1. For example, as shown, the mounting portion 130 of the control body 125 may include opposing guide rod receptacles 137 that are each slidably engaged with a respective one of the guide members 133 for at least partially constraining movement of the control body 125 to being linearly along the axial reference axis A1 such that the control body 125. In these regards, the control body 125 is an example of a linear movement body.

The cleaning member movement mechanism 122 includes a barrel cam 139 and a coupling element engaging body 141. The barrel cam 139 and the coupling element engaging body 141 may jointly define a two-part rotational movement body where the barrel cam 139 is a first body part of the rotational movement body and the coupling element engaging body 141 is a second body part of the rotational movement body. The barrel cam 139 may be engaged with a first end portion 132 of the main mounting body 131 for enabling rotation of the barrel cam 139 about the axial reference axis A1 and for inhibiting axial movement along the axial reference axis A1. The barrel cam 139 includes a groove 143 extending around its exterior surface. The groove preferably extends contiguously around the exterior surface of the barrel cam 139. An engagement member 125A of the control body 125 is positioned within (i.e., engaged with) the groove 143 whereby axial movement of the control body 125 causes a corresponding rotational movement of the barrel cam 139. A contour of the groove 143 (i.e., cam profile) defines rotational movement of the barrel cam 139 as a function of linear displacement of the control body 125 (i.e., a camming action).

Figures 4, 5:
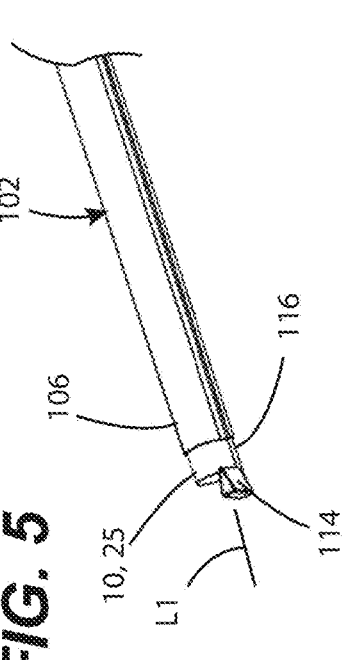
FIG. 4 is a perspective view of the imaging element cleaning apparatus shown in FIG. 2, where the cleaning member is in a deployed axial position and intermediate rotational position prior to imaging element engagement.
FIG. 5 is an enlarged partial view of the imaging element cleaning apparatus shown in FIG. 2, where the cleaning member is in a deployed axial position and intermediate rotational position prior to imaging element engagement.

The coupling element engaging body 141 is located within an interior space of the main mounting body 131 between the barrel cam 139 and a second end portion 134 of the main mounting body 131. The coupling element engaging body 141 includes a first end portion 141A, a second end portion 141B and a central portion 141C between the first and second end portions 141A, 141B. The first end portion 141A of the coupling element engaging body 141 is engaged with the barrel cam 139 for inhibiting relative rotational movement between the barrel cam 139 and the coupling element engaging body 141 and permitting axial displacement therebetween. The second end portion 141B of the coupling element engaging body 141 has a proximate end portion of the coupling element 116 fixedly engaged thereto such that rotation of the coupling element engaging body 141 causes a corresponding rotation of the coupling element 116 and, thus, the cleaning member 114. The central portion 141C of the coupling element engaging body 141 includes an engagement member 141D that engages a camming structure 138 (e.g., one or more raised, contoured ribs) on an adjacent interior surface of the main mounting body 131 for enabling rotation of the coupling element engaging body 141 to cause a corresponding axial displacement of the coupling element engaging body 141. Such axial displacement of the coupling element engaging body 141 facilitates movement of the cleaning member 114 between the stowed axial position S (FIGS. 2-3) and the deployed axial position D (FIG. 4), as discussed above. Such axial movement of the coupling element engaging body 141 and associated axial movement of the cleaning member 114 are achieved through joint rotational movement of the barrel cam 139 and the coupling element engaging body 141 whereby, as shown in FIG. 4-5, the cleaning member 114 preferably achieves the deployed axial position D at a rotational position between the home rotational position P1-114 (i.e., an intermediate rotational position) and the cleaning member 114 engaging the imaging element. To this end, a contour of the camming structure 138 at least partially defines axial displacement of the coupling element engaging body 141 as a function of rotational displacement of the coupling element engaging body 141.

Figures 9A, 9B:
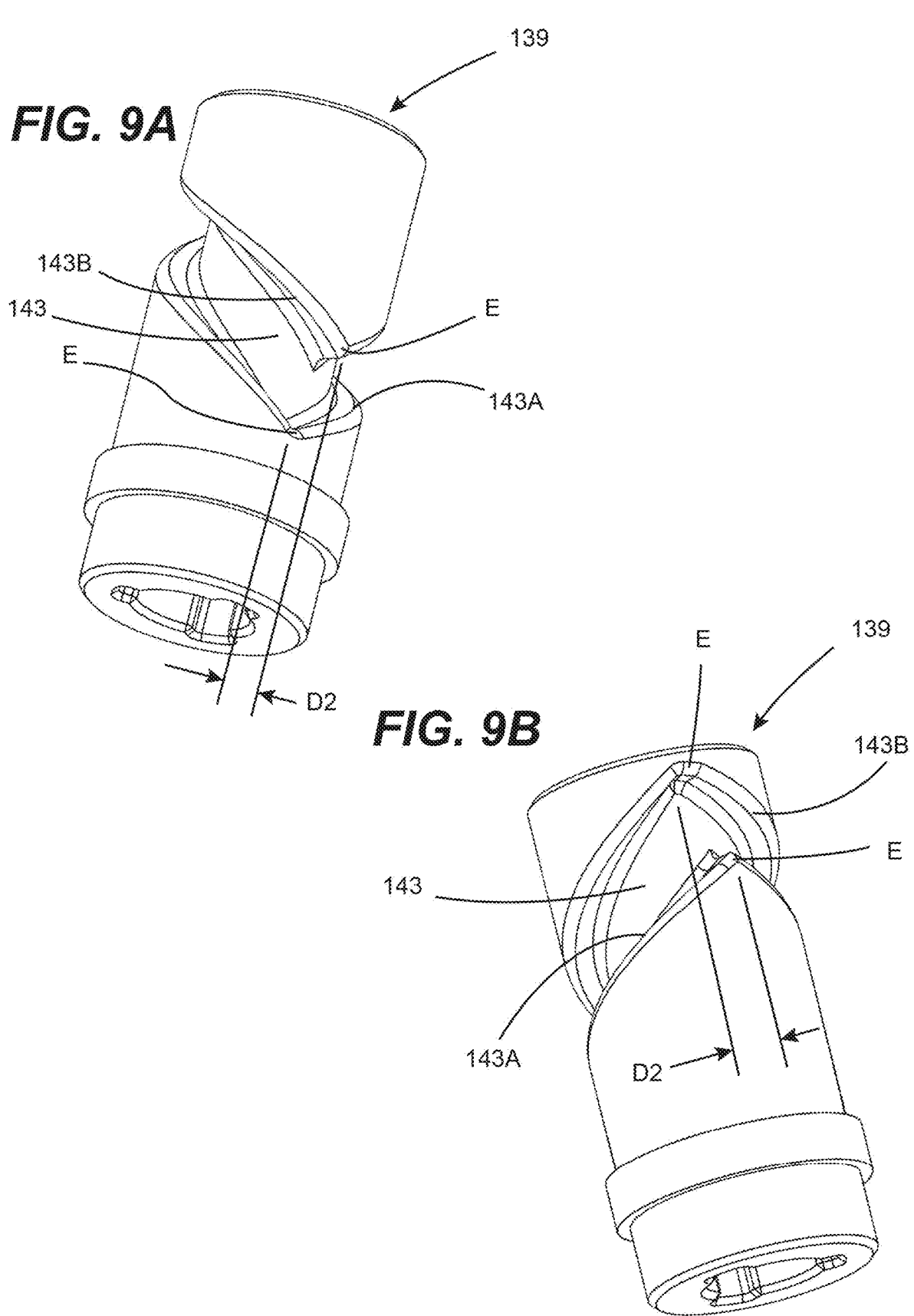
FIG. 9A is a first perspective view of a barrel cam of the imaging element cleaning apparatus shown in FIG. 2.
FIG. 9B is a second perspective view of the barrel cam of the imaging element cleaning apparatus shown in FIG. 2.

In operation, a single instance of the control body 125 being moved from the at-rest position P1-125 (FIGS. 2-4) to the fully-displaced position P2-125 (FIG. 6) and then back to the at-rest position P1-125 (FIGS. 2-4) causes the cleaning member 114 to correspondingly rotate in a first rotational direction (e.g., clockwise as viewed from the user interface body 103) from the home rotational position P1-114 (FIGS. 2-4) to the displaced rotational position P2-114 (FIG. 6) and then back to the home rotational position P1-114. To this end, as best shown in FIGS. 8B, 9A, and 9B, the groove 143 of the barrel cam 139 may be bound by a first perimeter edge portion 143A and a second perimeter edge portion 143B. In preferred embodiments, the first perimeter edge portion 143A and the second perimeter edge portion 143B have the same profile but may have adjacent end points E offset by an angular distance D2.

During movement of the control body 125 from the at-rest position P1-125 to the fully-displaced position P2-125, the engagement member 125A of the control body 125 engages the first perimeter edge portion 143A of the groove 143 for urging the barrel cam 139 to rotate in the first rotational direction from a first (i.e., home) rotational position placing the cleaning member 114 in the home rotational position P1-114 (FIGS. 2-4) to a second (i.e., displaced) rotational position placing the cleaning member 114 in the displaced rotational position P2-114 (FIG. 6). During movement of the control body 125 from the fully-displaced position P2-125 to the at-rest position P1-125, the engagement member 125A of the control body 125 engages the second perimeter edge portion 143B of the groove 143 for urging the barrel cam 139 to rotate in the first rotational direction from the second rotational position to the first rotational position. Accordingly, in these respects, the profiles and relative positions of the first and second perimeter edge portions 143A, 143B at least partially define rotational movement of the barrel cam 139 and thus corresponding rotational movement the cleaning member 114 as a function of axial movement of the control body 125.

Movement of the control body 125 from the at-rest position P1-125 (FIGS. 2-4) to the fully-displaced position P2-125 is manually energized by a user of the cleaning apparatus 100, whereas movement of the control body 125 from the fully-displaced position P2-125 to the at-rest position P1-125 is advantageously provided by force exerted by the springs 135. To this end, each instance of manual force application for moving the control body 125 from the at rest position P1-125 to the fully-displaced position P2-125 causing the barrel cam 139 to rotationally move from a first position in which the cleaning member 114 is in the rotational position P1-114 to a second position placing the cleaning member 114 in the displaced rotational position P2-114 and serves to compress the springs 135 to generate stored energy in the springs 135. The stored energy causes the springs 135 to deliver force to the control body 125 as manual force application on the control body 125 is released for thereby urging the control body 125 from the fully-displaced position P2-125 to the at-rest position P1-125 during which the barrel cam 139 is correspondingly rotated in the first rotational direction from the second position to the first position to cause the cleaning member 114 to correspondingly move from the displaced rotational position P2-114 to the home rotational position P1-114. Advantageously, in view of such spring-force assisted control body actuation and placement of the control body 125 on the user interface body 103, a user may employ one-handed operation of the cleaning apparatus 100 and endoscope engaged therewith.

FIGS. 10-17 illustrate various aspects of an imaging element cleaning apparatus configured in accordance with a second embodiment of the disclosures made herein, which is designated as the cleaning apparatus 200. The cleaning apparatus 200 has the same underlying applicability and operability as the cleaning apparatus 100 discussed above in reference to FIGS. 2-9. Specifically, the cleaning apparatus 200 similarly offers one-handed operation of the cleaning apparatus 200 and endoscope engaged therewith. The key difference between the cleaning apparatus 100 and the cleaning apparatus 200 is that the user-manipulated body for actuating instances of the lens cleaning operation is in the form of a lever as opposed to a button. For conciseness of disclosure, only the aspects of the cleaning apparatus 200 that are operationally different than that of the cleaning apparatus 100 will be described. Components of the cleaning apparatus 200 that are similar to components of the cleaning apparatus 100 will be designated by similar reference numerals—e.g., linear movement body 225 of the cleaning apparatus 200 correspond to control body 125 of the cleaning body 100.

The cleaning apparatus 200 includes a control lever 226 having a first end portion 226A, a second end portion 226B, and a central portion 226C between the first end second end portions 226A, 226B. The control lever 226 is pivotably engaged at the first end portion 226A to the main mounting body 231. For example, as shown, the control lever 226 is pivotally engaged with main mounting body 231 and is pivotable coupled at its central portion 226C to the linear movement body 225 via a control lever linkage member 227. Thus, pivotal movement of the control lever 226 results in linear movement of the linear movement body 225 along the axial reference axis A1.

Figures 14, 15, 16, 17:
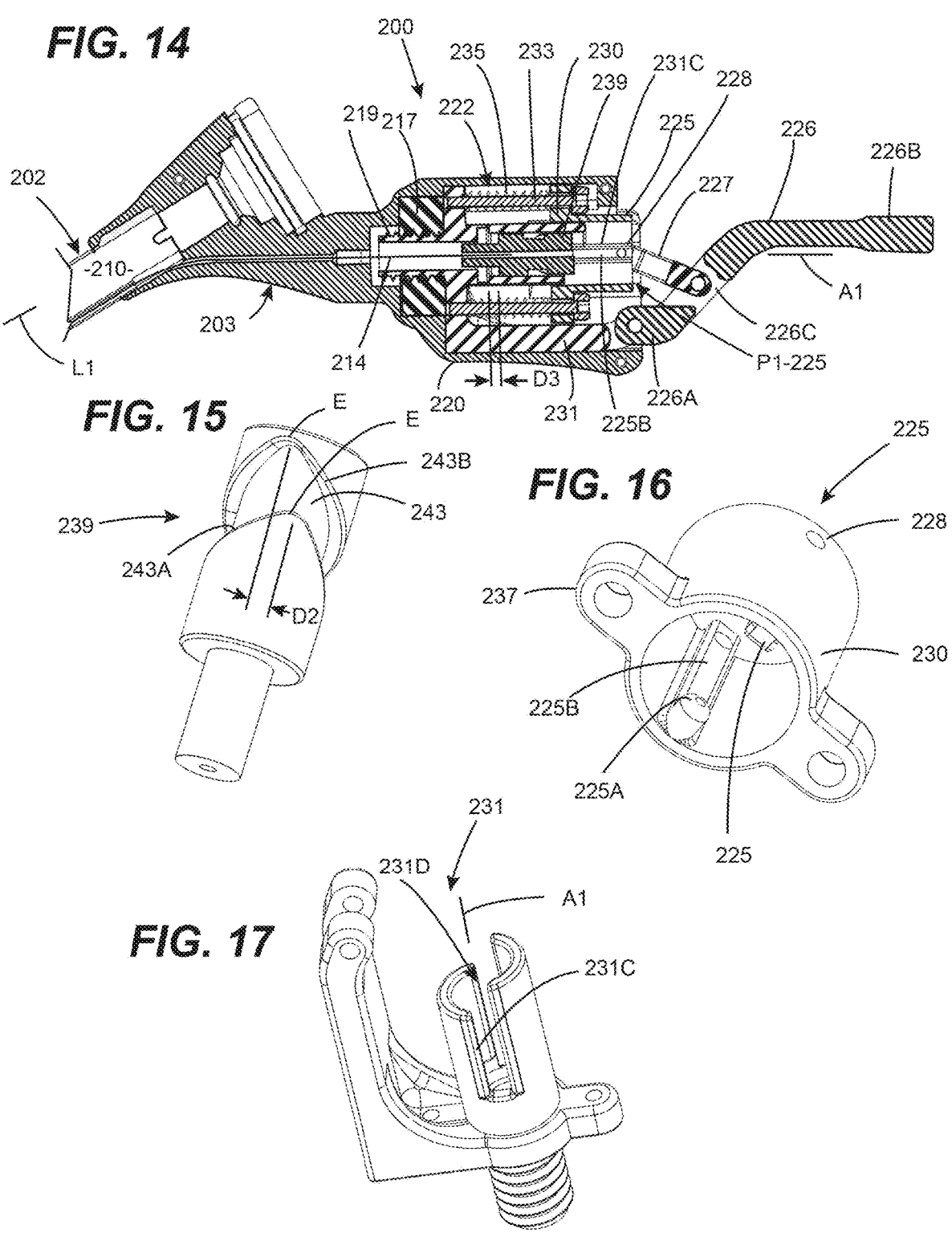
FIG. 14 is a cross-sectional view taken along the line 14-14 in FIG. 10.
FIG. 15 is a perspective view of a barrel cam of the imaging element cleaning apparatus shown in FIG. 10.
FIG. 16 is a perspective view of a linear movement body of the imaging element cleaning apparatus shown in FIG. 10.
FIG. 17 is a perspective view of a main mounting body of the imaging element cleaning apparatus shown in FIG. 10.

Referring now, to FIGS. 14 and 16, the linear movement body 225 includes a lever coupling portion 228 and a mounting portion 230 connected to the lever coupling portion 228. The control lever 226 is engaged with the lever coupling portion 228 via the control lever linkage member 227. The mounting portion 230 is translatably engaged with a main mounting body 231 of the cleaning member movement mechanism 222. The main mounting body 231 is located within an interior space of the user interface body 203 and is fixedly engaged with the user interface body 203. Alternatively, the main mounting body 231 may be unitarily formed with the user interface body 203.

The cleaning member movement mechanism 222 includes guide members 233 and springs 235 (i.e., resilient biasing members). The guide members 233 are in a spaced-apart arrangement and are each engaged with a respective portion of the main mounting body 231. Each of the springs 235 is associated with one of the guide members 233. The mounting portion 230 of the linear movement body 225 is engaged with the guide members 233 and the springs 235 to jointly bias the linear movement body 225 to the at-rest position P1-225. Engagement of the mounting portion 230 of the linear movement body 225 with the guide members 233 at least partially constrains movement of the linear movement body 225 to being along the axial reference axis A1. For example, as shown, the mounting portion 230 of the linear movement body 225 may include opposing guide rod receptacles 237 that are each slidably engaged with a respective one of the guide members 233 for at least partially constraining movement (e.g., limiting unrestricted movement) of the linear movement body 225 to being linearly along the axial reference axis A1 such that the linear movement body 225 may be a linear movement body. For further constraining or entirely constraining) movement of the linear movement body 225 to being linear along the axial reference axis A1, the linear movement body 225 may include guide members 225B that engage within guide channels 231C of the main mounting body 231.

The cleaning member movement mechanism 222 includes a barrel cam 239 rotatable engaged within a central passage 231D of the main mounting body 231 (FIG. 17) for enabling rotation of the barrel cam 239 about the axial reference axis A1. The barrel cam 239 includes a groove 243 extending around its exterior surface. An engagement member 225A of the linear movement body 225 is positioned within (i.e., engaged with) the groove 243 whereby axial movement of the linear movement body 225 causes a corresponding rotational movement of the barrel cam 239. A contour of the groove 243 (i.e., cam profile) defines rotational movement of the barrel cam 239 as a function of linear displacement of the linear movement body 225 (i.e., a camming action). A proximate end portion of the coupling element 216 is fixedly engaged with the barrel cam 239 such that rotation of the barrel cam 239 causes corresponding rotational movement of the coupling element 216 and, thus, the cleaning member 214.

In operation, it is preferred for a single instance of the linear movement body 225 being moved from the at-rest position P1-225 (FIGS. 10, 11 and 14) to a fully-displaced position P2-225 (FIG. 12) and then back to the at-rest position P1-225 to cause the cleaning member 214 to correspondingly rotate in a first rotational direction (e.g., counterclockwise as viewed from the user interface body 203 (although the barrel cam 239 may be designed for clockwise rotation) from a home rotational position P1-214 (FIGS. 10 and 11) to a displaced rotational position P2-214 (FIG. 12) and then back to the home rotational position P1-214. To this end, as shown in FIG. 15, the groove 243 of the barrel cam 239 may be bound by a first perimeter edge portion 243A and a second perimeter edge portion 243B. In some embodiments, the first perimeter edge portion 243A and the second perimeter edge portion 243B have different profiles to accommodate manual force exertion during displacement toward the fully-displaced position P2-225 (FIG. 12) and spring-applied force during displacement toward the at-rest position P1-225. In some embodiments, the first perimeter edge portion 243A and the second perimeter edge portion 243B may have adjacent end points E offset by an angular distance D2. Similar to the barrel cam 139 of the cleaning apparatus 100, the barrel cam 239 of the cleaning apparatus 200 has perimeter edge portions with end points corresponding to the at-rest position P1-225 and the fully-displaced position P2-225 (e.g., rotationally spaced by about 180 degrees).

During movement of the linear movement body 225 from the at-rest position P1-225 (FIG. 10) to the fully-displaced position P2-225 (FIG. 12), the engagement member 225A of the linear movement body 225 engages the first perimeter edge portion 243A of the groove 243 for urging the barrel cam 239 to rotate in the first rotational direction from a first rotational position placing the cleaning member 214 in the home rotational position P1-214 to a second rotational position placing the cleaning member 214 in displaced rotational position P2-214. During movement of the linear movement body 225 from the fully-displaced position P2-225 to the at-rest position P1-225, the engagement member 225A of the linear movement body 225 engages the second perimeter edge portion 243B of the groove 243 for urging the barrel cam 239 to rotate in the first rotational direction from the second rotational position to the first rotational position. Accordingly, in these respects, the profiles and relative positions of the first and second perimeter edge portions 243A, 243B at least partially define rotational movement of the barrel cam 239 and thus corresponding rotational movement the cleaning member 214 as a function of axial movement of the linear movement body 225.

Figures 10, 11:
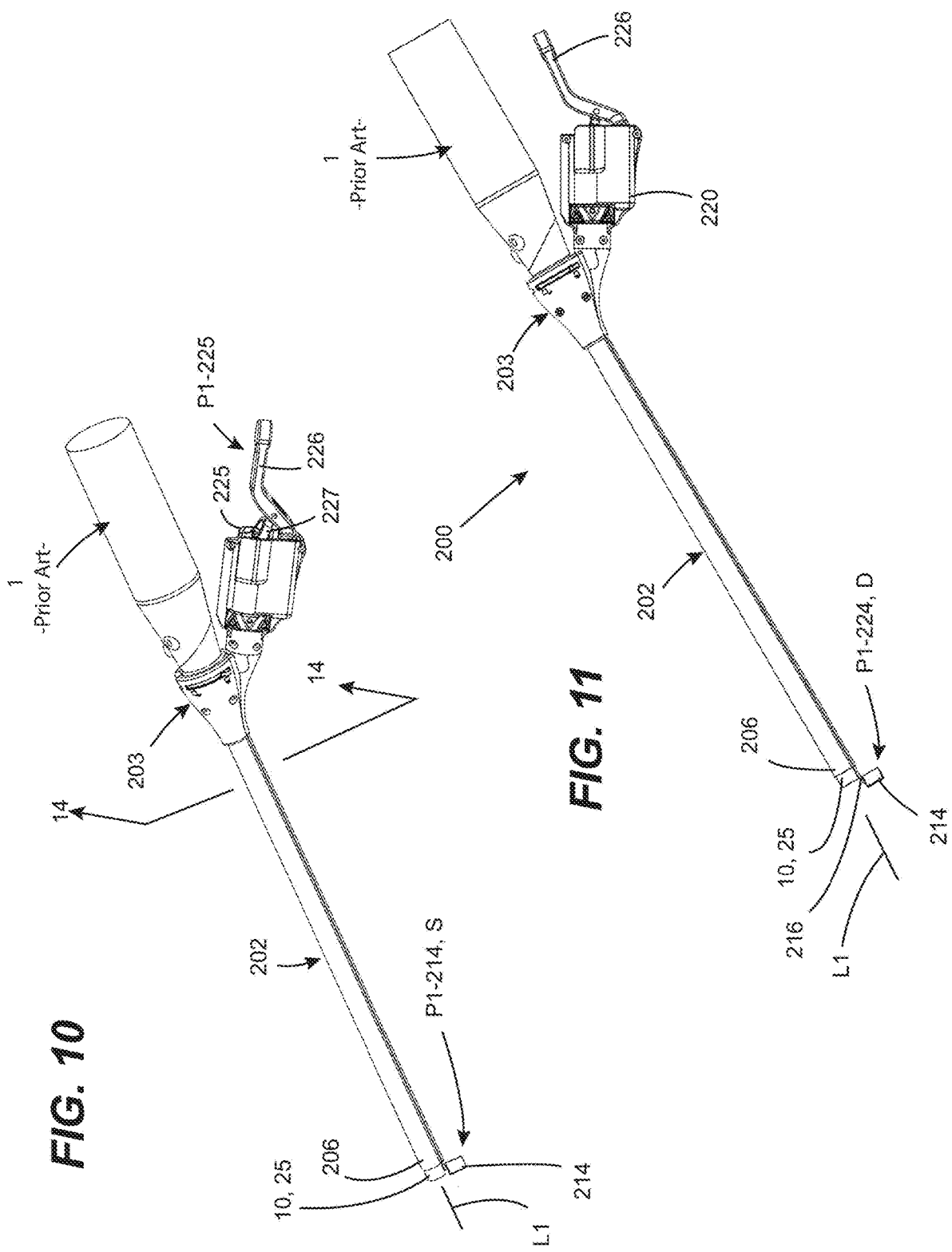
FIG. 10 is a perspective view showing an imaging element cleaning apparatus in accordance with a second embodiments of the disclosures made herein, where a cleaning member of the imaging element cleaning apparatus is in a stowed axial position and a home rotational position.
FIG. 11 is a perspective view showing the imaging element cleaning apparatus shown in FIG. 10, in accordance with a second embodiments of the disclosures made herein, where the cleaning member is in a deployed axial position and the home rotational position prior to imaging element engagement.
Figures 12, 13:
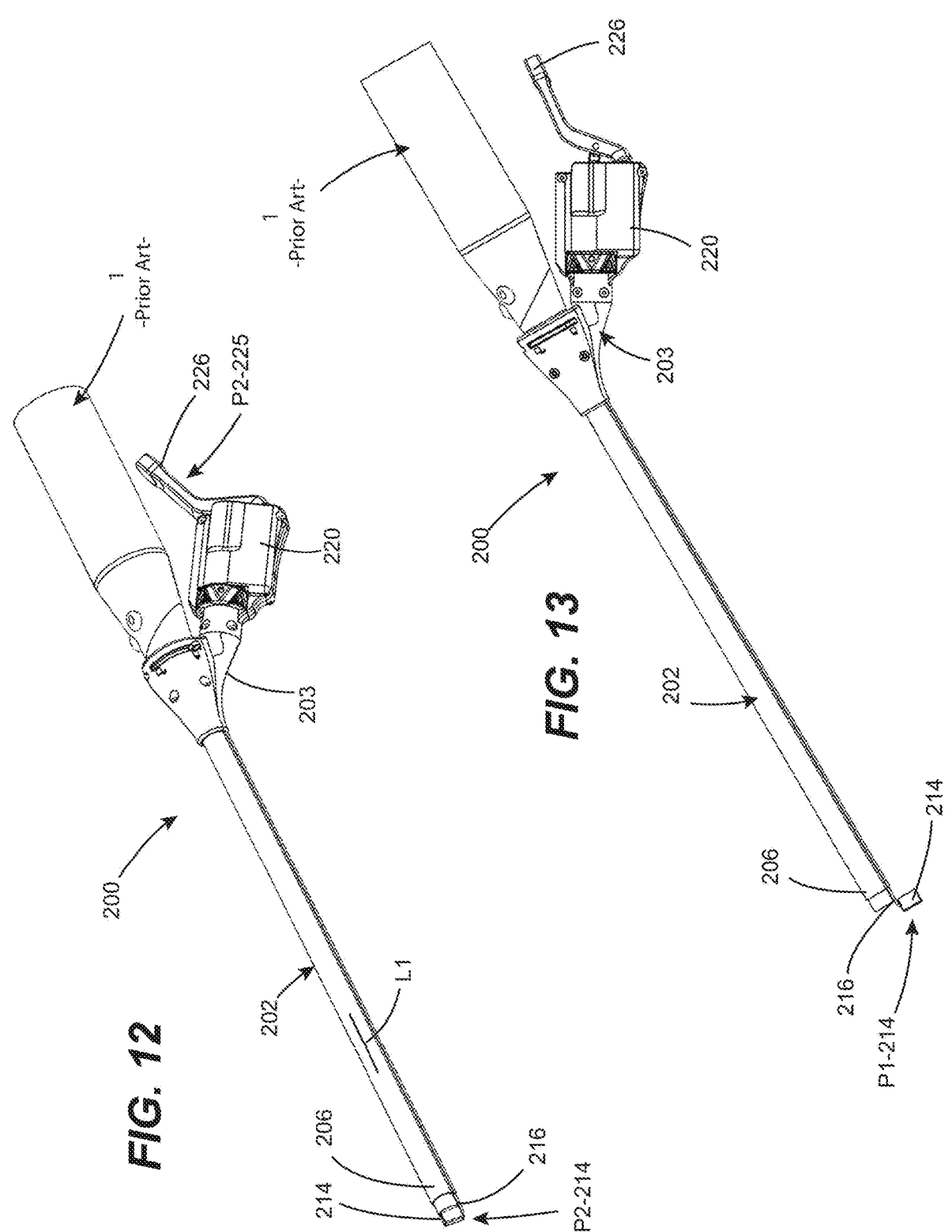
FIG. 12 is a perspective view of the imaging element cleaning apparatus shown in FIG. 10, where the cleaning member is in the deployed axial position and a fully-displaced rotational position.
FIG. 13 is a perspective view of the imaging element cleaning apparatus shown in FIG. 10, where the cleaning member is in the deployed axial position and the home rotational position after imaging element engagement.

In some embodiments, as shown in FIGS. 10 and 11, movement for providing an instance of imaging element cleaning by the cleaning member 214 includes (e.g., prior to or in conjunction with) the cleaning member 214 moving axially from a stowed axial position S (FIG. 10) to a deployed axial position D (FIG. 11) relative to the distal end position 206 of the elongated body 202 and the cleaning member 214 returning to the stowed axial position S in conjunction with or after returning to the home rotational position P1-214. To this end, as shown in FIG. 14, the barrel cam 239 may be slidably engaged with the main mounting body 231 for enabling pivotal movement of the control lever 226 and associated axial movement of the linear movement body 225 to correspondingly cause axial movement of the barrel cam 239 by a distance D3 (FIG. 14) that is equal to an axial distance between the stowed axial position S and the deployed axial position D. Such axial movement of the barrel cam 239 and associated axial movement of the cleaning member 214 are achieved without any associated rotational movement whereby the cleaning member 214 achieves deployed axial position D while still in the home rotational position P1-214. Details and benefits of the stowed axial position S are discussed above in reference to the cleaning apparatus 100.

In view of the disclosures made herein, a skilled person will appreciate that the control lever 226 may be implemented in a manner whereby the control lever 226 is in direct engagement with the linear movement body 225 (i.e., a form of a bush button). In this manner, pivoting action of the control lever 226 may cause the control lever 226 to directly exert a force upon the linear movement body 225 such that the linear movement body 225 moves from the at-rest position P1-225 to the fully-displaced position P2-225. Advantageously, this embodiment eliminates the control lever linkage member 227.

Figure 18:
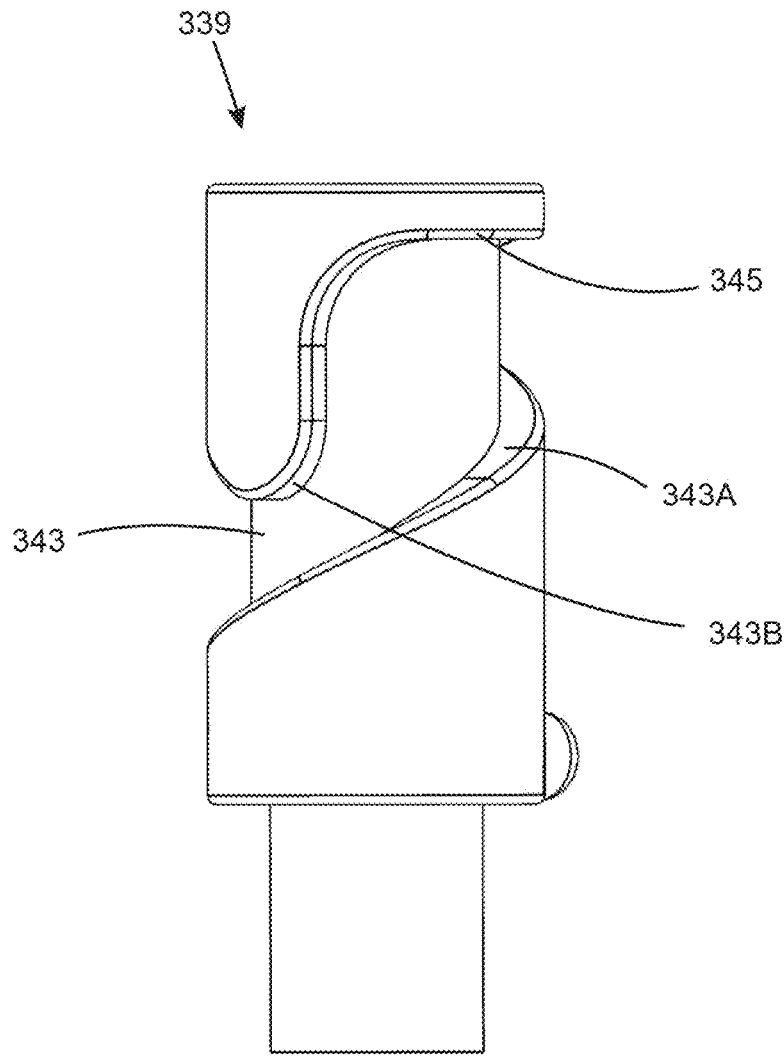
FIG. 18 is a side view showing a barrel cam in accordance with a third embodiment of the disclosures made herein.

FIG. 18 is a side view showing a barrel cam in accordance with a third embodiment of the disclosures made herein (i.e., barrel cam 339). The barrel cam 339 includes structural attributes for inhibiting reverse rotational movement (i.e., movement against an intended rotational direction). To this end, the groove 343 of the barrel cam 339 is defined by asymmetric first and second perimeter edge portions 343A, 343B. The description of the barrel 300 is presented in the context of being a replacement for the barrel cam 239 in the cleaning apparatus 200.

As shown, the first perimeter edge portion 343A may be configured in the same or a functionally similar way as for the barrel cam 239 discussed above in reference to FIGS. 14 and 15—i.e., engagement of the first perimeter edge portion 343A by the engagement member 225A of the linear movement body 225 during movement from the at-rest position P1-225 toward the fully-displaced position P2-225 causes a corresponding rotational movement of the barrel cam 339 in the first rotational direction. However, the second perimeter edge portion 343B of the barrel cam 339 that opposes the segment of the first perimeter edge portion 343A that enables rotational movement of the cam body 339 in response to movement of the linear movement body 225 from the at-rest position P1-225 toward the fully-displaced position P2-225 includes truncated portion 345.

The truncated portion 345 extends substantially perpendicular to a rotational axis of the barrel cam 339. Accordingly, partial movement of the linear movement body 225 from its at-rest position P1-225 toward its fully-displaced position and then return to its at-rest position does not result in corresponding reverse rotational movement of the cam body 339 (i.e., rotational movement opposite the first rotational direction). Instead, further rotational movement of the barrel cam 339 required full displacement of the linear movement body 225 from its at-rest position P1-225 to its fully-displaced position P2-225, thereby enabling the engagement member 225A of the linear movement body 225 to engage the segment of the second perimeter edge portion 343B of the barrel cam 339 (i.e., the inclined segment) that enables further rotation of the barrel cam 339 in the first rotational direction. Such anti-rotational feature is beneficial to ensure full operational rotation of the cleaning member 214 (e.g., 360-degree rotation), particularly in view of reverse rotation of the cleaning member 214 potentially contributing to redepositing of contaminants (e.g., smearing) from the cleaning member 214 back on to the associated imaging element.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An imaging element cleaning apparatus, comprising:
   a chassis engageable with an endoscope to retain the endoscope in a fixed seated position relative to the chassis;
   a cleaning member at a distal end portion of the chassis;
   a coupling element attached at a distal end portion thereof to the cleaning member whereby rotational movement of the coupling element causes corresponding rotational movement of the cleaning member; and
   a cleaning member movement mechanism at a proximate end portion of the chassis, wherein the cleaning member movement mechanism includes a rotational movement body and a linear movement body moveably coupled to the rotational movement body, wherein the rotational movement body and the linear movement body are jointly configured whereby linear movement of the linear movement body from an at-rest position to a fully-displaced position and back to the at-rest position causes the rotational movement body to correspondingly rotate in a first rotational direction from a home rotational position to a displaced rotational position and back to the home rotational position, and wherein the rotational movement body is coupled to a proximate end portion of the coupling element for enabling said rotation of the rotational movement body to correspondingly cause said rotational movement of the coupling element.

2. The apparatus of claim 1 wherein the rotational movement body is coupled to the linear movement body though a camming structure that defines rotational movement of the rotational movement body as a function of linear displacement of the linear movement body.

3. The apparatus of claim 1 wherein:
the rotational movement body includes a groove extending contiguously around an outer surface of the rotational movement body;
a contour of the groove defines rotational movement of the rotational movement body as a function of linear displacement of the linear movement body; and
an engagement member of the linear movement body is positioned within the groove.

4. The apparatus of claim 1 wherein:
the cleaning member movement mechanism includes a control lever having a first end portion, a second end portion, and a central portion between the first end second end portions;
the cleaning member movement mechanism includes a main mounting body one of engaged with the chassis and unitarily formed with the chassis;
the control lever is pivotably engaged at the first end portion thereof to at least one of the chassis and the main mounting body; and
the control lever is pivotable coupled at the central portion thereof to the linear movement body.

5. The apparatus of claim 4 wherein:
the cleaning member movement mechanism includes a control lever linkage member; and
the control lever is pivotable engaged at the central portion thereof to the linear movement body by the control lever linkage member.

6. The apparatus of claim 4 wherein:
the linear movement body is constrained to linear movement along an axial reference axis; and
at least one of the main mounting body and the linear movement body constrains rotational movement of the rotational movement body to being about the axial reference axis.

7. The apparatus of claim 4 wherein the rotational movement body is coupled to the linear movement body though a camming structure that defines rotational movement of the rotational movement body as a function of linear displacement of the linear movement body.

8. The apparatus of claim 7 wherein:
the cleaning member movement mechanism includes a control lever linkage member; and
the control lever is pivotable engaged at the central portion thereof to the linear movement body by the control lever linkage member.

9. The apparatus of claim 4 wherein:
the rotational movement body includes a groove extending contiguously around an outer surface of the rotational movement body;
a contour of the groove defines rotational movement of the rotational movement body as a function of linear displacement of the linear movement body; and an engagement member of the linear movement body is positioned within the groove.

10. The apparatus of claim 1 wherein:
the cleaning member movement mechanism includes a main mounting body one of engaged with the chassis and unitarily formed with the chassis;
the linear movement body is constrained to linear movement along an axial reference axis; and
at least one of the main mounting body and the linear movement body constrains rotational movement of the rotational movement body to being about the axial reference axis.

11. The apparatus of claim 10 wherein the rotational movement body is coupled to the linear movement body though a camming structure that defines rotational movement of the rotational movement body as a function of linear displacement of the linear movement body.

12. The apparatus of claim 10 wherein:
the rotational movement body includes a groove extending contiguously around an outer surface of the rotational movement body;
a contour of the groove defines rotational movement of the rotational movement body as a function of linear displacement of the linear movement body; and
an engagement member of the linear movement body is positioned within the groove.

13. The apparatus of claim 1 wherein the rotational movement body being coupled to the proximate end portion of the coupling member includes the rotational movement body being attached directly to the proximate end portion of the coupling member.

14. The apparatus of claim 13 wherein:
the cleaning member movement mechanism includes a main mounting body one of engaged with the chassis and unitarily formed with the chassis;
the linear movement body is constrained to linear movement along an axial reference axis;
at least one of the main mounting body and the linear movement body constrains rotational movement of the rotational movement body to being about the axial reference axis;
the rotational movement body is slidably engaged with the linear movement body for enabling axial translation along the axial reference axis;
axial translation of the linear movement body from the at-rest position to the fully-displaced position causes the rotational movement body to axially translate from a first position placing the cleaning element in a stowing position to a second position placing the cleaning member in a deployed position; and
axial translation of the linear movement body from the fully-displaced position to the at-rest position causes the rotational movement body to axially translate from the second position to the first position.

15. The apparatus of claim 14 wherein:
the rotational movement body is a two part body including a first body part and a second body part;
the first body part of the rotational movement body is coupled to the linear movement body though a camming structure that defines rotational movement of the first body part of the rotational movement body as a function of linear displacement of the linear movement body;
the first body part is moveably coupled to the second body part for enabling relative axial displacement therebetween;

the coupling element is attached directly to the second body part;

said axial translation of the linear movement body from the at-rest position to the fully-displaced position causes the second body part of the rotational movement body to axially translate from a first position placing the cleaning member in the stowing position to a second position placing the cleaning member in the deployed position; and said axial translation of the linear movement body from the fully-displaced position to the at-rest position causes the second body part of the rotational movement body to axially translate from the second position to the first position.

16. An imaging element cleaning apparatus, comprising:

a chassis engageable with an endoscope whereby the endoscope is retained in a fixed seated position relative to the chassis;

a cleaning member at a distal end portion of the chassis;

a coupling element attached at a distal end portion thereof to the cleaning member whereby rotational movement of the coupling element causes a corresponding rotational movement of the cleaning member; and a cleaning member movement mechanism at a proximate end portion of the chassis, wherein the cleaning member movement mechanism includes a rotational movement body and a linear movement body moveably coupled to the rotational movement body, wherein the rotational movement body includes a groove extending contiguously around an outer surface of the rotational movement body, wherein the linear movement body includes an engagement member positioned within the groove, wherein the linear movement body is biased to an at-rest position and is constrained to linear movement, wherein the linear movement body is moveable along an axial reference axis between the at-rest position and a fully-displaced position, wherein the groove is bound by a first perimeter edge portion thereof and a second perimeter edge portion thereof, wherein movement of the linear movement body toward the fully-displaced position causes the linear movement body to engage the first perimeter edge portion and movement of the linear movement body away from the fully-displaced position causes the linear movement body to engage the second perimeter edge portion, wherein a profile of the first perimeter edge portion and a profile of the second perimeter edge portion jointly enable linear movement of the linear movement body from the at-rest position to the fully-displaced position and back to the at-rest position to cause the rotational movement body to correspondingly rotate in a first rotational direction from a first rotational position placing the cleaning member in the home rotational position to a second rotational position placing the cleaning member in the displaced rotational position and back to the first rotational position, and wherein the rotational movement body is coupled to a proximate end portion of the coupling element for enabling said rotation of the rotational movement body to corresponding causes said rotational movement of the coupling element.

17. The apparatus of claim 16 wherein:

the cleaning member movement mechanism includes a control lever having a first end portion, a second end portion, and a central portion between the first end second end portions;

the control lever is pivotably engaged at the first end portion thereof to at least one of the chassis and a main mounting body of the cleaning member movement mechanism; and the control lever is pivotable engaged at the central portion thereof to the linear movement body.

18. The apparatus of claim 16 wherein the rotational movement body being coupled to the proximate end portion of the coupling member includes the rotational movement body being attached directly to the proximate end portion of the coupling member.

19. The apparatus of claim 18 wherein:

the cleaning member movement mechanism includes a main mounting body one of engaged with the chassis and unitarily formed with the chassis;

the linear movement body is constrained to linear movement along an axial reference axis;

at least one of the main mounting body and the linear movement body constrains rotational movement of the rotational movement body to being about the axial reference axis;

the rotational movement body is slidably engaged with the linear movement body for enabling axial translation along the axial reference axis;

axial translation of the linear movement body from the at-rest position to the fully-displaced position causes the rotational movement body to axially translate from a first position placing the cleaning member in the stowing position to a second position placing the cleaning member in the deployed position; and axial translation of the linear movement body from the fully-displaced position to the at-rest position causes the rotational movement body to axially translate from the second position to the first position.

20. The apparatus of claim 19 wherein:

the rotational movement body is a two part body including a first body part and a second body part;

the first body part includes a groove extending contiguously around an outer surface thereof;

a contour of the groove defines rotational movement of the rotational movement body as a function of linear displacement of the linear movement body;

an engagement member of the linear movement body is positioned within the groove;

the first body part is moveably coupled to the second body part for enabling relative axial displacement therebetween;

the rotational movement body is attached directly to the second body part;

said axial translation of the linear movement body from the at-rest position to the fully-displaced position causes the second body part of the rotational movement body to axially translate from a first position placing the cleaning member in the stowing position to a second position placing the cleaning member in the deployed position; and said axial translation of the linear movement body from the fully-displaced position to the at-rest position causes the second body part of the rotational movement body to axially translate from the second position to the first position.

21. The apparatus of claim 16 wherein the second perimeter edge portion includes a truncated portion for inhibiting reverse rotation of the barrel in response to movement of the linear movement body toward the at-rest position.

* * * * *